United States Patent
Talbot et al.

(10) Patent No.: US 12,059,204 B2
(45) Date of Patent: Aug. 13, 2024

(54) SYSTEM, METHOD AND COMPUTER-READABLE STORAGE DEVICE FOR CONTROLLING LASER LIGHT SOURCE OF LITHOTRIPSY DEVICE

(71) Applicant: GYRUS ACMI, INC., Southborough, MA (US)

(72) Inventors: Brian M. Talbot, Southborough, MA (US); Kurt G. Shelton, Bedford, MA (US); Anne G. McLoughlin, Southborough, MA (US); Masayasu Chida, Tokyo (JP)

(73) Assignee: Gyrus ACMI, Inc., Westborough, MA (US)

( * ) Notice: Subject to any disclaimer, the term of this patent is extended or adjusted under 35 U.S.C. 154(b) by 961 days.

(21) Appl. No.: 16/968,801

(22) PCT Filed: Feb. 9, 2019

(86) PCT No.: PCT/US2019/017391
§ 371 (c)(1),
(2) Date: Aug. 10, 2020

(87) PCT Pub. No.: WO2019/157406
PCT Pub. Date: Aug. 15, 2019

(65) Prior Publication Data
US 2021/0045812 A1 Feb. 18, 2021

Related U.S. Application Data

(60) Provisional application No. 62/628,513, filed on Feb. 9, 2018.

(51) Int. Cl.
*A61B 18/26* (2006.01)
*A61B 1/00* (2006.01)
(Continued)

(52) U.S. Cl.
CPC .......... *A61B 18/26* (2013.01); *A61B 1/00006* (2013.01); *A61B 1/00055* (2013.01);
(Continued)

(58) Field of Classification Search
None
See application file for complete search history.

(56) References Cited

U.S. PATENT DOCUMENTS

| 4,971,034 A | 11/1990 | Doi et al. |
| 5,785,702 A * | 7/1998 | Murphy-Chutorian ..................... A61B 18/24 606/7 |

(Continued)

FOREIGN PATENT DOCUMENTS

| CA | 2734120 C | 9/2016 |
| CN | 1249162 | 4/2000 |

(Continued)

OTHER PUBLICATIONS

"Iteration." Merriam-Webster.com Dictionary, Merriam-Webster, https://www.merriam-webster.com/dictionary/iteration. Accessed Dec. 5, 2023. (Year: 2023).*

(Continued)

*Primary Examiner* — Carl H Layno
*Assistant Examiner* — Manolis Pahakis
(74) *Attorney, Agent, or Firm* — Schwegman Lundberg & Woessner, P.A.

(57) ABSTRACT

System and methods for controlling a laser light source of a lithotripsy device to fragment or break a target object are disclosed. An exemplary system includes a controller that can perform one or more iterations of a first process, and one or more iterations of a second process. The first process includes steps of selecting at least one variable operating parameter of a laser light source of a lithotripsy device, (Continued)

determining a value of each of a plurality of base settings of the at least one variable operating parameter selected and selecting one of the plurality of base settings based on signals received from the target in response to laser irradiation according to the value of each of the plurality of base settings set. The second process includes controlling the laser light source based on the one of the plurality of base settings selected.

14 Claims, 4 Drawing Sheets

(51) Int. Cl.
| | | |
|---|---|---|
| A61B 1/015 | (2006.01) | |
| A61B 1/018 | (2006.01) | |
| A61B 1/05 | (2006.01) | |
| A61B 1/06 | (2006.01) | |
| A61B 1/12 | (2006.01) | |
| A61B 1/307 | (2006.01) | |
| A61B 1/31 | (2006.01) | |
| A61B 17/3207 | (2006.01) | |
| A61B 18/00 | (2006.01) | |
| A61B 18/24 | (2006.01) | |
| A61M 1/00 | (2006.01) | |
| H01S 3/067 | (2006.01) | |
| H01S 3/16 | (2006.01) | |

(52) U.S. Cl.
CPC .......... *A61B 1/00087* (2013.01); *A61B 1/015* (2013.01); *A61B 1/018* (2013.01); *A61B 1/06* (2013.01); *A61B 1/126* (2013.01); *A61B 1/307* (2013.01); *A61B 1/31* (2013.01); *A61B 18/24* (2013.01); *A61M 1/74* (2021.05); *A61M 1/77* (2021.05); *H01S 3/06716* (2013.01); *A61B 1/00045* (2013.01); *A61B 1/00105* (2013.01); *A61B 1/05* (2013.01); *A61B 17/320783* (2013.01); *A61B 2018/00482* (2013.01); *A61B 2018/00505* (2013.01); *A61B 2018/00511* (2013.01); *A61B 2018/00559* (2013.01); *A61B 2018/00642* (2013.01); *A61B 2018/00672* (2013.01); *A61B 2018/00678* (2013.01); *A61B 2018/00696* (2013.01); *A61B 2018/00702* (2013.01); *A61B 2018/00773* (2013.01); *A61B 2018/00982* (2013.01); *A61B 2217/005* (2013.01); *A61B 2217/007* (2013.01); *A61B 2562/0247* (2013.01); *A61M 2205/3334* (2013.01); *A61M 2205/3344* (2013.01); *H01S 3/1616* (2013.01)

(56) References Cited

U.S. PATENT DOCUMENTS

| | | | |
|---|---|---|---|
| 5,931,834 A * | 8/1999 | Murphy-Chutorian ...................... A61B 18/24 606/7 | |
| 6,156,049 A | 12/2000 | Lovato et al. | |
| 6,527,716 B1 * | 3/2003 | Eppstein ................ A61N 1/325 604/20 | |
| 8,109,872 B2 | 2/2012 | Kennedy, II et al. | |
| 9,259,231 B2 | 2/2016 | Navve et al. | |
| 9,308,315 B2 | 4/2016 | Stubkjaer et al. | |
| 9,597,160 B1 * | 3/2017 | Gregg, II ............... A61B 34/25 | |
| 9,907,563 B2 | 3/2018 | Germain et al. | |
| 10,201,382 B2 * | 2/2019 | Wiener ................ H10N 30/802 | |
| 10,441,345 B2 * | 10/2019 | Aldridge ........ A61B 17/320092 | |
| 2003/0036751 A1 | 2/2003 | Anderson et al. | |
| 2004/0229295 A1 * | 11/2004 | Marchitto ................ A61N 1/30 435/7.5 | |
| 2005/0222535 A1 | 10/2005 | Uesugi et al. | |
| 2006/0047185 A1 | 3/2006 | Shener et al. | |
| 2006/0264995 A1 | 11/2006 | Fanton et al. | |
| 2008/0154185 A1 | 6/2008 | Blight | |
| 2008/0300662 A1 * | 12/2008 | Taylor ................... A61B 18/24 372/25 | |
| 2009/0058996 A1 | 3/2009 | Mitsuhashi | |
| 2009/0156900 A1 | 6/2009 | Robertson | |
| 2010/0004510 A1 | 1/2010 | Kuroshima | |
| 2010/0049119 A1 | 2/2010 | Norman et al. | |
| 2010/0076304 A1 | 3/2010 | Teramura | |
| 2011/0082449 A1 | 4/2011 | Melsky et al. | |
| 2011/0237880 A1 | 9/2011 | Hamel et al. | |
| 2012/0116168 A1 | 5/2012 | Moellstam et al. | |
| 2013/0303852 A1 | 11/2013 | Hiraga et al. | |
| 2015/0119645 A1 | 4/2015 | Baldwin | |
| 2015/0133728 A1 | 5/2015 | Finkman et al. | |
| 2015/0216394 A1 | 8/2015 | Toyoda | |
| 2015/0230864 A1 | 8/2015 | Xuan et al. | |
| 2015/0320303 A1 | 11/2015 | Kawase | |
| 2015/0320433 A1 * | 11/2015 | Navve ................ A61B 17/225 606/2.5 | |
| 2015/0342682 A1 | 12/2015 | Bowe | |
| 2016/0022126 A1 | 1/2016 | Ramesh et al. | |
| 2016/0022289 A1 | 1/2016 | Wan | |
| 2016/0135894 A1 | 5/2016 | Finkman et al. | |
| 2016/0157954 A1 | 6/2016 | Sagon et al. | |
| 2016/0206805 A1 | 7/2016 | Hassidov et al. | |
| 2016/0250075 A1 * | 9/2016 | Kawai ................ A61F 9/00825 606/6 | |
| 2017/0112572 A1 * | 4/2017 | Shazly ................ A61B 18/20 | |
| 2017/0215989 A1 * | 8/2017 | Gregg, II ............. A61C 8/0006 | |
| 2017/0220754 A1 | 8/2017 | Harrah et al. | |
| 2017/0325890 A1 * | 11/2017 | Chia ................ A61B 5/0084 | |
| 2018/0084980 A1 | 3/2018 | Watanabe et al. | |
| 2018/0168439 A1 | 6/2018 | Hibbs et al. | |
| 2018/0289394 A1 | 10/2018 | Shah | |
| 2018/0325622 A1 * | 11/2018 | Groves, Jr. .......... A61C 1/0046 | |
| 2019/0008545 A1 | 1/2019 | Stulen et al. | |
| 2019/0134279 A1 | 5/2019 | Benamou et al. | |
| 2019/0247566 A1 | 8/2019 | Hassidov et al. | |
| 2019/0282073 A1 | 9/2019 | Truckai | |
| 2020/0000522 A1 * | 1/2020 | Chia ..................... A61B 18/26 | |
| 2020/0187761 A1 | 6/2020 | Shelton | |
| 2020/0187768 A1 | 6/2020 | Shelton et al. | |
| 2020/0330157 A1 * | 10/2020 | Junger ................... A61B 18/22 | |
| 2020/0405130 A9 | 12/2020 | Shelton | |
| 2021/0045811 A1 | 2/2021 | Shelton et al. | |
| 2021/0220529 A1 | 7/2021 | Wang | |
| 2021/0244267 A1 | 8/2021 | Shtul et al. | |

FOREIGN PATENT DOCUMENTS

| | | |
|---|---|---|
| CN | 101273915 | 10/2008 |
| CN | 104619281 | 5/2015 |
| CN | 106232037 | 12/2016 |
| CN | 106456368 | 2/2017 |
| CN | 111683580 A | 9/2020 |
| CN | 111683617 A | 9/2020 |
| CN | 115175626 A | 10/2022 |
| CN | 115334982 A | 11/2022 |
| DE | 112021001260 T5 | 12/2022 |
| DE | 112021001396 T5 | 12/2022 |
| EP | 0048410 A1 | 3/1982 |
| EP | 1086674 A1 | 3/2001 |
| EP | 3429453 A1 | 1/2019 |
| EP | 3749242 | 11/2021 |
| JP | S5971736 A | 4/1984 |
| JP | H03207371 | 9/1991 |
| JP | H08201026 A | 8/1996 |
| JP | 2003210485 | 7/2003 |
| JP | 2007244679 A | 9/2007 |
| JP | 2009506817 | 2/2009 |
| JP | 2010075314 A | 4/2010 |
| JP | 2016043178 | 4/2016 |
| JP | 2016515441 | 5/2016 |

(56) References Cited

FOREIGN PATENT DOCUMENTS

| | | |
|---|---|---|
| JP | 2016533830 A | 11/2016 |
| JP | 2017500172 A | 1/2017 |
| JP | 2017522058 A | 8/2017 |
| JP | 2019093138 | 6/2019 |
| JP | 7374911 | 10/2023 |
| WO | WO-2011032165 A2 | 3/2011 |
| WO | WO-2013099507 A1 | 7/2013 |
| WO | WO-2015029039 A1 | 3/2015 |
| WO | 2015069387 | 5/2015 |
| WO | WO-2019157247 A1 | 8/2019 |
| WO | WO-2019157406 A1 | 8/2019 |
| WO | WO-2019157247 A9 | 4/2020 |
| WO | WO-WO A9 2019157409 | 5/2020 |
| WO | WO-2021173775 A1 | 9/2021 |
| WO | WO-2021173791 A1 | 9/2021 |

OTHER PUBLICATIONS

"U.S. Appl. No. 16/968,800, Restriction Requirement mailed Apr. 5, 2023", 5 pgs.
"Indian Application Serial No. 202247046058, First Examination Report mailed Apr. 11, 2023", 6 pgs.
"U.S. Appl. No. 16/968,800, Response filed May 23, 2023 to Restriction Requirement mailed Apr. 5, 2023", 8 pgs.
"U.S. Appl. No. 16/803,649, Non Final Office Action mailed May 26, 2023", 22 pgs.
"Japanese Application Serial No. 2020-542995, Notification of Reasons for Refusal mailed May 22, 2023", w English translation, 8 pgs.
"U.S. Appl. No. 16/968,800, Non Final Office Action mailed Jun. 21, 2023", 13 pgs.
"Japanese Application Serial No. 2020-542770, Response filed Jun. 27, 2023 to Examiners Decision of Final Refusal mailed Feb. 27, 2023", with machine translation, 23 pgs.
"U.S. Appl. No. 16/803,612, Final Office Action mailed Jul. 24, 2023", 35 pgs.
"U.S. Appl. No. 16/803,612, Response filed Sep. 25, 2023 to Final Office Action mailed Jul. 24, 2023", 15 pgs.
"U.S. Appl. No. 16/803,649, Response filed Aug. 28, 2023 to Non Final Office Action mailed May 26, 2023", 13 pgs.
"U.S. Appl. No. 16/968,800, Response filed Sep. 21, 2023 to Non Final Office Action mailed Jun. 21, 2023", 13 pgs.
"Japanese Application Serial No. 2020-542995, Response filed Sep. 7, 2023 to Notification of Reasons for Refusal mailed May 22, 2023", w/ english claims, 9 pgs.
"Japanese Application Serial No. 2022-551708, Notification of Reasons for Refusal mailed Aug. 28, 2023", w/ English Translation, 9 pgs.
"International Application Serial No. PCT/US2015/045788, International Search Report mailed Nov. 3, 2015", 3 pgs.
"International Application Serial No. PCT/US2015/045788, Written Opinion mailed Nov. 3, 2015", 5 pgs.
"International Application Serial No. PCT/US2019/017153, International Search Report mailed Apr. 30, 2019", 2 pgs.
"International Application Serial No. PCT/US2019/017153, Written Opinion mailed Apr. 30, 2019", 6 pgs.
"U.S. Appl. No. 16/803,612, Examiner Interview Summary mailed Nov. 8, 2022", 3 pgs.
"U.S. Appl. No. 16/803,612, Final Office Action mailed Sep. 14, 2022", 34 pgs.
"U.S. Appl. No. 16/803,612, Response filed Nov. 8, 2022 to Final Office Action mailed Sep. 14, 2022", 18 pgs.
"U.S. Appl. No. 16/803,649, Examiner Interview Summary mailed Oct. 5, 2022", 3 pgs.
"U.S. Appl. No. 16/803,649, Response filed Oct. 4, 2022 to Non Final Office Action mailed Jul. 7, 2022", 15 pgs.
"International Application Serial No. PCT/US2021/019568, International Preliminary Report on Patentability mailed Sep. 9, 2022", 7 pgs.
"International Application Serial No. PCT/US2021/019599, International Preliminary Report on Patentability mailed Sep. 9, 2022", 7 pgs.
"U.S. Appl. No. 16/803,649, Non Final Office Action mailed Jul. 7, 2022", 15 pgs.
U.S. Appl. No. 16/803,612, filed Feb. 27, 2020, Endoscope Unclogging System and Method.
U.S. Appl. No. 16/803,649, filed Feb. 27, 2020, Suction and Irrigation Control System and Method.
U.S. Appl. No. 16/968,800, filed Aug. 10, 2020, Medical Laser Apparatus and System.
"European Application Serial No. 19750838.5, Extended European Search Report mailed Oct. 1, 2021", 8 pgs.
"International Application Serial No. PCT/US2021/019568, International Search Report mailed May 14, 2021", 4 pgs.
"International Application Serial No. PCT/US2021/019568, Written Opinion mailed May 14, 2021", 5 pgs.
"International Application Serial No. PCT/US2021/019599, International Search Report mailed May 19, 2021", 5 pgs.
"International Application Serial No. PCT/US2021/019599, Written Opinion mailed May 19, 2021", 5 pgs.
"U.S. Appl. No. 16/803,612, Examiner Interview Summary mailed Jun. 3, 2022", 3 pgs.
"U.S. Appl. No. 16/803,612, Non Final Office Action mailed Mar. 7, 2022", 38 pgs.
"U.S. Appl. No. 16/803,612, Response filed May 31, 2022 to Non Final Office Action mailed Mar. 7, 2022", 25 pgs.
"U.S. Appl. No. 16/803,649, Response filed Apr. 14, 2022 to Restriction Requirement mailed Feb. 16, 2022", 8 pgs.
"European Application Serial No. 19750838.5, Response filed Apr. 28, 2022 to Communication pursuant to Rules 70(2) and 70a(2) EPC mailed Oct. 19, 2021", 16 pgs.
"European Application Serial No. 19750838.5, Response filed Apr. 28, 2022 to Extended European Search Report mailed Oct. 1, 2021", 16 pgs.
"European Application Serial No. 19750915.1, Response filed Jun. 9, 2022 to Extended European Search Report mailed Nov. 22, 2021", 10 pgs.
"Korean Application Serial No. 10-2020-7026082, Voluntary Amendment Filed Jan. 11, 2022", w/English Claims, 15 pgs.
"European Application Serial No. 19750838.5, Response filed Mar. 13, 2021", 17 pgs.
"European Application Serial No. 19750915.1, Response filed Mar. 16, 2021", 9 pgs.
"International Application Serial No. PCT/US2019/017391, International Preliminary Report on Patentability mailed Aug. 20, 2020", 8 pgs.
"U.S. Appl. No. 16/803,649, Restriction Requirement mailed Feb. 16, 2022", 6 pgs.
"European Application Serial No. 19750915.1, Extended European Search Report mailed Nov. 22, 2021", 8 pgs.
"U.S. Appl. No. 16/803,612, Advisory Action mailed Dec. 1, 2022", 3 pgs.
"U.S. Appl. No. 16/803,612, Examiner Interview Summary mailed Mar. 28, 2023", 3 pgs.
"U.S. Appl. No. 16/803,612, Non Final Office Action mailed Dec. 28, 2022", 32 pgs.
"U.S. Appl. No. 16/803,612, Response filed Mar. 23, 2023 to Non Final Office Action mailed Dec. 28, 2022", 14 pgs.
"U.S. Appl. No. 16/803,612, Response filed Dec. 9, 2022 to Advisory Action mailed Dec. 1, 2022", 17 pgs.
"U.S. Appl. No. 16/803,649, Advisory Action mailed Mar. 24, 2023", 5 pgs.
"U.S. Appl. No. 16/803,649, Examiner Interview Summary mailed Feb. 21, 2023", 2 pgs.
"U.S. Appl. No. 16/803,649, Final Office Action mailed Dec. 22, 2022", 17 pgs.
"U.S. Appl. No. 16/803,649, Response filed Feb. 21, 2023 to Final Office Action mailed Dec. 22, 2022", 12 pgs.
"Japanese Application Serial No. 2020-542770, Examiners Decision of Final Refusal mailed Feb. 27, 2023", w/ English Translation, 7 pgs.

(56) References Cited

OTHER PUBLICATIONS

"Japanese Application Serial No. 2020-542770, Notification of Reasons for Refusal mailed Nov. 14, 2022", w/ English translation, 14 pgs.

"Japanese Application Serial No. 2020-542770, Response filed Feb. 10, 2023 to Notification of Reasons for Refusal mailed Nov. 14, 2022", with machine translation, 24 pgs.

"Japanese Application Serial No. 2020-542995, Notification of Reasons for Rejection mailed Nov. 7, 2022", w/ English Translation, 9 pgs.

"Japanese Application Serial No. 2020-542995, Response filed Feb. 3, 2023 to Notification of Reasons for Rejection mailed Nov. 7, 2022", with English claims, 10 pgs.

"U.S. Appl. No. 16/803,612, Advisory Action mailed Oct. 5, 2023", 3 pgs.

"Indian Application Serial No. 202247046058, Response filed Oct. 4, 2023 to Office Action mailed Apr. 11, 2023", 24 pgs.

"Mexican Application Serial No. MX a 2020 008318, Office Action mailed Aug. 31, 2023", with machine translation, 9 pgs.

"U.S. Appl. No. 16/803,612, Response filed Oct. 24, 2023 to Advisory Action mailed Oct. 5, 2023", 14 pgs.

"Japanese Application Serial No. 2022-551708, Response filed Oct. 13, 2023 to Notification of Reasons for Refusal mailed Aug. 28, 2023", with English claims, 12 pgs.

"Canadian Application Serial No. 3,169,535, Examiners Rule 86(2) Requisition mailed Sep. 29, 2023", 4 pgs.

"Canadian Application Serial No. 3,169,549, Examiners Rule 86(2) Report mailed Sep. 29, 2023", 4 pgs.

"U.S. Appl. No. 16/803,612, Non Final Office Action mailed Nov. 8, 2023", 26 pgs.

"Australian Application Serial No. 2019216954, First Examination Report mailed Oct. 23, 2023", 4 pgs.

"Japanese Application Serial No. 2022-551714, Notification of Reasons for Refusal mailed Oct. 23, 2023", w English Translation, 15 pgs.

"Chinese Application Serial No. 201980012090.7, Office Action mailed Nov. 3, 2023", W English Translation, 25 pgs.

"U.S. Appl. No. 16/968,800, Final Office Action mailed Nov. 30, 2023", 13 pgs.

"Australian Application Serial No. 2019217992, First Examination Report mailed Nov. 22, 2023", 4 pgs.

"Mexican Application Serial No. MX a 2020 008318, Response filed Nov. 16, 2023 to Office Action mailed Aug. 31, 2023", with machine translation, 23 pgs.

"U.S. Appl. No. 16/803,612, Corrected Notice of Allowability mailed Feb. 28, 2024", 6 pgs.

"U.S. Appl. No. 16/803,612, Examiner Interview Summary mailed Feb. 8, 2024", 3 pgs.

"U.S. Appl. No. 16/803,612, Notice of Allowance mailed Feb. 14, 2024", 9 pgs.

"U.S. Appl. No. 16/803,612, Response filed Feb. 5, 2024 to Non Final Office Action mailed Nov. 8, 2023", 15 pgs.

"U.S. Appl. No. 16/803,649, Advisory Action mailed Feb. 13, 2024", 3 pgs.

"U.S. Appl. No. 16/803,649, Examiner Interview Summary mailed Feb. 6, 2024", 3 pgs.

"U.S. Appl. No. 16/803,649, Final Office Action mailed Dec. 13, 2023", 24 pgs.

"U.S. Appl. No. 16/803,649, Response filed Feb. 2, 2024 to Final Office Action mailed Dec. 13, 2023", 13 pgs.

"U.S. Appl. No. 16/968,800, Examiner Interview Summary mailed Jan. 31, 2024", 3 pgs.

"U.S. Appl. No. 16/968,800, Notice of Allowance mailed Feb. 14, 2024", 8 pgs.

"U.S. Appl. No. 16/968,800, Response filed Jan. 25, 2024 to Final Office Action mailed Nov. 30, 2023", 12 pgs.

"Australian Application Serial No. 2019216954, Response filed Jan. 8, 2024 to First or Subsequent Examiner Report mailed Oct. 23, 2023", 22 pgs.

"Canadian Application Serial No. 3,169,535, Response filed Jan. 25, 2024 to Examiners Rule 86(2) Requisition mailed Sep. 29, 2023", 16 pgs.

"Canadian Application Serial No. 3, 169,549, Response filed Jan. 29, 2024 to Examiners Rule 86(2) Report mailed Sep. 29, 2023", 19 pgs.

"Chinese Application Serial No. 201980012086.0, First Office Action mailed Jan. 15, 2024", with English translation, 21 pgs.

"Chinese Application Serial No. 201980012090.7, Response filed Dec. 27, 2023 to Office Action mailed Nov. 3, 2023", with English claims, 16 pgs.

"European Application Serial No. 19750838.5, Communication Pursuant to Article 94(3) EPC mailed Feb. 8, 2024", 3 pgs.

"Japanese Application Serial No. 2022-551708, Examiners Decision of Final Refusal mailed Jan. 15, 2024", W/English Translation, 6 pgs.

"Japanese Application Serial No. 2022-551714, Response filed Dec. 18, 2023 to Notification of Reasons for Refusal mailed Oct. 23, 2023", with English claims, 10 pgs.

"Japanese Application Serial No. 2023-105314, Voluntary Amendment mailed Dec. 15, 2023", with machine translation, 9 pgs.

"Korean Application Serial No. 10-2020-7026082, Notice of Preliminary Rejection mailed Dec. 21, 2023", with machine translation, 6 pgs.

"Korean Application Serial No. 10-2020-7026082, Response filed Feb. 16, 2024 to Notice of Preliminary Rejection mailed Dec. 21, 2023", w/ english claims, 24 pgs.

"Korean Application Serial No. 2020-7025950, Notice of Preliminary Rejection mailed Jan. 30, 2024", with machine translation, 16 pgs.

"Australian Application Serial No. 2019217992, Response filed Mar. 26, 2024 to First Examination Report mailed Nov. 22, 2023", 21 pgs.

"Japanese Application Serial No. 2022-551714, Notification of Reasons for Rejection mailed Mar. 4, 2024", W English Translation, 8 pgs.

* cited by examiner

SYSTEM, METHOD AND COMPUTER-READABLE STORAGE DEVICE FOR CONTROLLING LASER LIGHT SOURCE OF LITHOTRIPSY DEVICE

CROSS-REFERENCE TO RELATED APPLICATION

This application is a U.S. National Stage Filing under 35 U.S.C. 371 from International Application No. PCT/US2019/017391, filed on Feb. 9, 2019, and published as WO 2019/157406 on Aug. 15, 2019 which claims the benefit of U.S. Provisional Application No. 62/628,513, filed on Feb. 9, 2018, the entire contents of which are incorporated herein by reference in their entireties.

BACKGROUND

Field

The invention relates generally to a system, method and computer-readable storage device storing instructions for controlling a laser light source of a lithotripsy device to fragment or break a target object such as a calculus or a stone.

Description of Related Art

Calculi or stones are hard masses that form in the urinary tract and may cause pain, bleeding, inflection and/or blockage of the flow of urine. Smaller calculi or stones may cause no symptoms and may be passed in urine from the kidneys and through the urinary tract on their own. Larger calculi or stones that do not pass on their own can be removed with lithotripsy. Lithotripsy can involve use of an endoscope such as a ureteroscope. The endoscope can be inserted through the urethra, into the bladder, up the ureter and into the collecting system of the kidney to reach the calculi or stones. The endoscope can include an imaging device to provide images for guiding the insertion of the endoscope and to visualize the calculi or stones. In some instances, the endoscope can be used with a device inserted through a working channel of the endoscope and out of a distal opening of the working channel to fragment or break a larger calculus or stone into smaller pieces that can be removed with the endoscope or passed in urine. One such device includes an optical fiber for outputting a laser light as an energy source for fragmenting or breaking the calculus or stone.

A calculus or stone can be made of minerals in the urine that form crystals. The calculus or stone can be composed mainly of calcium. However, the calculus or stone can be composed of other substances such as uric acid, cystine, or struvites (a mixture of magnesium, ammonium and phosphate).

The mechanism by which a calculus or stone forms may result in the calculus or stone having a homogenous composition or a heterogeneous composition. A calculus or stone having a homogenous composition is more likely to have a substantially consistent mechanical property throughout the calculus or stone. Such a calculus or stone may be more easily fragmented or broken with laser light having a single set of operating parameters (e.g., energy, peak power, pulse width, average power, and frequency). In contrast, a calculus or stone having a heterogeneous composition is more likely to have a variety of mechanical properties. Such a calculus or stone may be harder to fragment or break with laser light having a single set of operating parameters. Therefore, a need exists for a technique to more effectively and efficiently fragment or break a calculus or stone having a variety of mechanical properties.

SUMMARY

One embodiment of the invention provides a system comprising: a controller configured to: perform one or more iterations of a first process, wherein in the first process the controller is configured to: select at least one variable operating parameter of a laser light source of a lithotripsy device; determine a value of each of a plurality of base settings of the at least one variable operating parameter selected; and perform, in order, for the each of the plurality of base settings: set the at least one variable operating parameter selected to the value of the each of the plurality of base settings; and control the laser light source to output laser light based on the value of the each of the plurality of base settings set; select one of the plurality of base settings of the at least one variable operating parameter selected; and perform one or more iterations of a second process, wherein in the second process, the controller is configured to control the laser light source based on the one of the plurality of base settings of the at least one variable operating parameter selected.

Another embodiment of the invention provides a method comprising: performing one or more iterations of a first process, wherein the first process comprises: selecting at least one variable operating parameter of a laser light source of a lithotripsy device; determining a value of each of a plurality of base settings of the at least one variable operating parameter selected; and performing, in order, for the each of the plurality of base settings: setting the at least one variable operating parameter selected to the value of the each of the plurality of base settings; and controlling the laser light source to output laser light based on the value of the each of the plurality of base settings set; selecting one of the plurality of base settings of the at least one variable operating parameter selected; and performing one or more iterations of a second process, wherein the second process comprises controlling the laser light source based on the one of the plurality of base settings of the at least one variable operating parameter selected.

Another embodiment of the invention provides a computer-readable storage device storing instructions that cause a computer of a controller to: perform one or more iterations of a first process, wherein in the first process the computer is configured to: select at least one variable operating parameter of a laser light source of a lithotripsy device; determine a value of each of a plurality of base settings of the at least one variable operating parameter selected; and perform, in order, for the each of the plurality of base settings: set the at least one variable operating parameter selected to the value of the each of the plurality of base settings; and control the laser light source to output laser light based on the value of the each of the plurality of base settings set; select one of the plurality of base settings of the at least one variable operating parameter selected; and perform one or more iterations of a second process, wherein in the second process, the computer is configured to control the laser light source based on the one of the plurality of base settings of the at least one variable operating parameter selected.

DETAILED DESCRIPTION

A system 1 according to one embodiment of the present invention will now be described with reference to the drawings.

Figure 1:
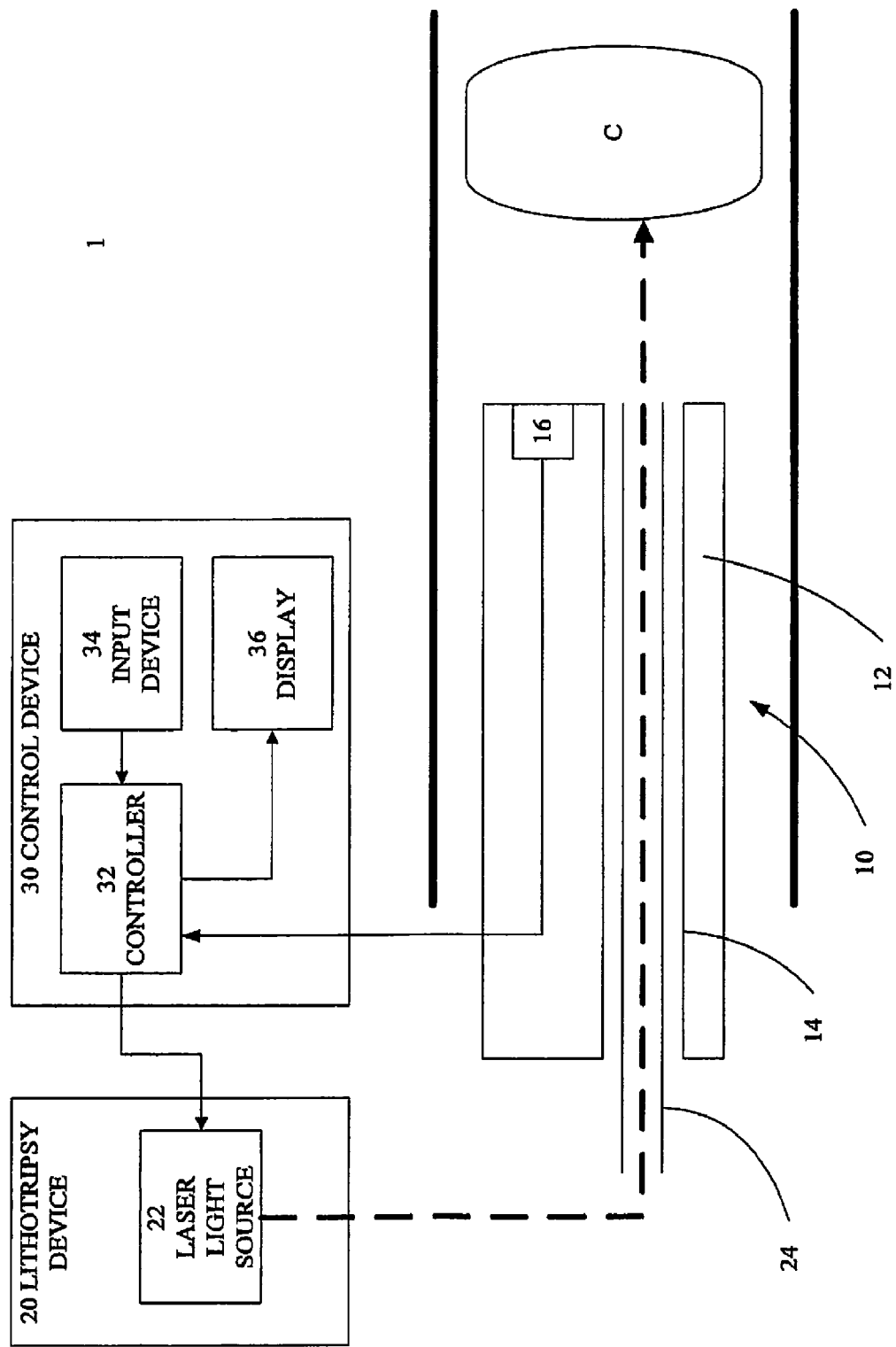
FIG. 1 is a schematic illustration of a system including an endoscope device, a lithotripsy device and a control device for fragmenting a calculus in a body lumen, according to an embodiment of the present system.

As shown in FIG. 1, the system 1 can include an endoscope device 10, a lithotripsy device 20 and a control device 30, the details of each of which will be described below.

The system 1 can be used in a medical procedure on a body lumen of a subject in order to fragment or break calculi (or stones) in the body lumen. As an example, the body lumen can be a bladder, a ureter or a collecting system of a kidney. However, the system 1 can be used to fragment or break calculi from substantially any body lumen, or from a non-human lumen.

The endoscope device 10 can include an insertion portion 12 having a distal end, where the insertion portion 12 can be sized and provided with sufficient flexibility to be inserted through the urethra, into the bladder, up the ureter and into the collecting system of the kidney to reach a calculus C (or stone). The insertion portion 12 can define a working channel 14 extending through at least a part of the insertion portion 12 to an opening at the distal end of the insertion portion 12. The working channel 14 can be shaped to allow structures such as a treatment instrument or a portion of the lithotripsy device 20 (as described in more detail below) to pass therethrough and past the opening.

The endoscope device 10 can include a light source (not illustrated) and an image sensor 16. The light source of the endoscope device 10 can output a light such as visible light to illuminate the interior of the body lumen and the calculus C. The image sensor 16 can photoconvert returning light incident on an imaging surface of the image sensor 16 into an image signal to be image processed by the control device 30 into an image. By this means, the image sensor 16 and the control device 30 can generate a plurality of images (or a video) over time.

The lithotripsy device 20 can include a laser light source 22 that can output a laser light under the control of the control device 30. The laser light source 22 can be, for example, a holmium (Ho) laser light source, a hulium: YAG (Ho:YAG) laser light source, a neodymium-doped:YAG (nd:YAG) laser light source, a semiconductor laser diode, a potassium-titanyl phosphate crystal (KTP) laser light source, a carbon dioxide (CO2) laser light source, an argon laser light source, an Excimer laser light source, a diode laser light source or another suitable laser light source.

The laser light source 22 can be controlled by the control device 30 to vary one or more operating parameters of the laser light. Operating parameters of the laser light include, but are not limited to energy (E) of the laser light, peak power ($P_{peak}$) of the laser light, pulse width (PW) of the laser light, average power ($P_{avg}$) of the laser light, and y (F) of the laser light.

The operating parameters are related by at least the following equations:

EQUATION 1:

$$E=P_{peak}*PW$$

EQUATION 2:

$$P_{avg}=E*F=P_{peak}*PW*F$$

The lithotripsy device 20 can further include a light fiber 24 that can be inserted through the working channel 14 of the endoscope device 10 to extend past the opening of the working channel 14. The light fiber 24 can transmit the laser light generated by the laser light source 22 to irradiate the calculus C. Absorbed energy from the laser light can cause the calculus C to fragment or break.

The control device 30 can include a controller 32, an input device 34 and a display 36.

The controller 32 can include a processor comprising hardware, and a storage comprising hardware (e.g., a memory). The functions of the processor may be implemented by respective pieces of hardware or may be implemented by an integrated piece of hardware, for example. The hardware may include one or a plurality of circuit devices (e.g., an integrated circuit (IC)) or one or a plurality of circuit elements (e.g., a resistor, a capacitor, etc) on a circuit board, for example. The processor can be one or more central processing units (CPUs), for example, but this should not be construed in a limiting sense, and various types of processors including a graphics processing unit (GPU) and a digital signal processor (DSP) may be used. The processor may be a hardware circuit with an application-specific integrated circuit (ASIC). The storage comprising hardware may be a semiconductor memory such as a static random-access memory (SRAM) and a dynamic random access memory (DRAM), a register, a magnetic storage device such as a hard disk device, and an optical storage device such as an optical disk device. The storage stores computer-readable instructions, for example. When the instructions are executed by the processor, the functions of the controller 32 described herein are implemented.

The controller 32 can control the imaging device 20 and the lithotripsy device 20 by the techniques described in detail below.

The input device 34 can include a device that can receive inputs from a user. The input device 34 can include a pointing device, a touch screen, a keypad and non-tactile entities such as voice control.

Processes that can be performed by the controller 32 in cooperation with the input device 34, the display 36, the endoscope device 10 and the lithotripsy device 20 are described in detail below with reference to FIGS. 2 and 3.

Figure 2:
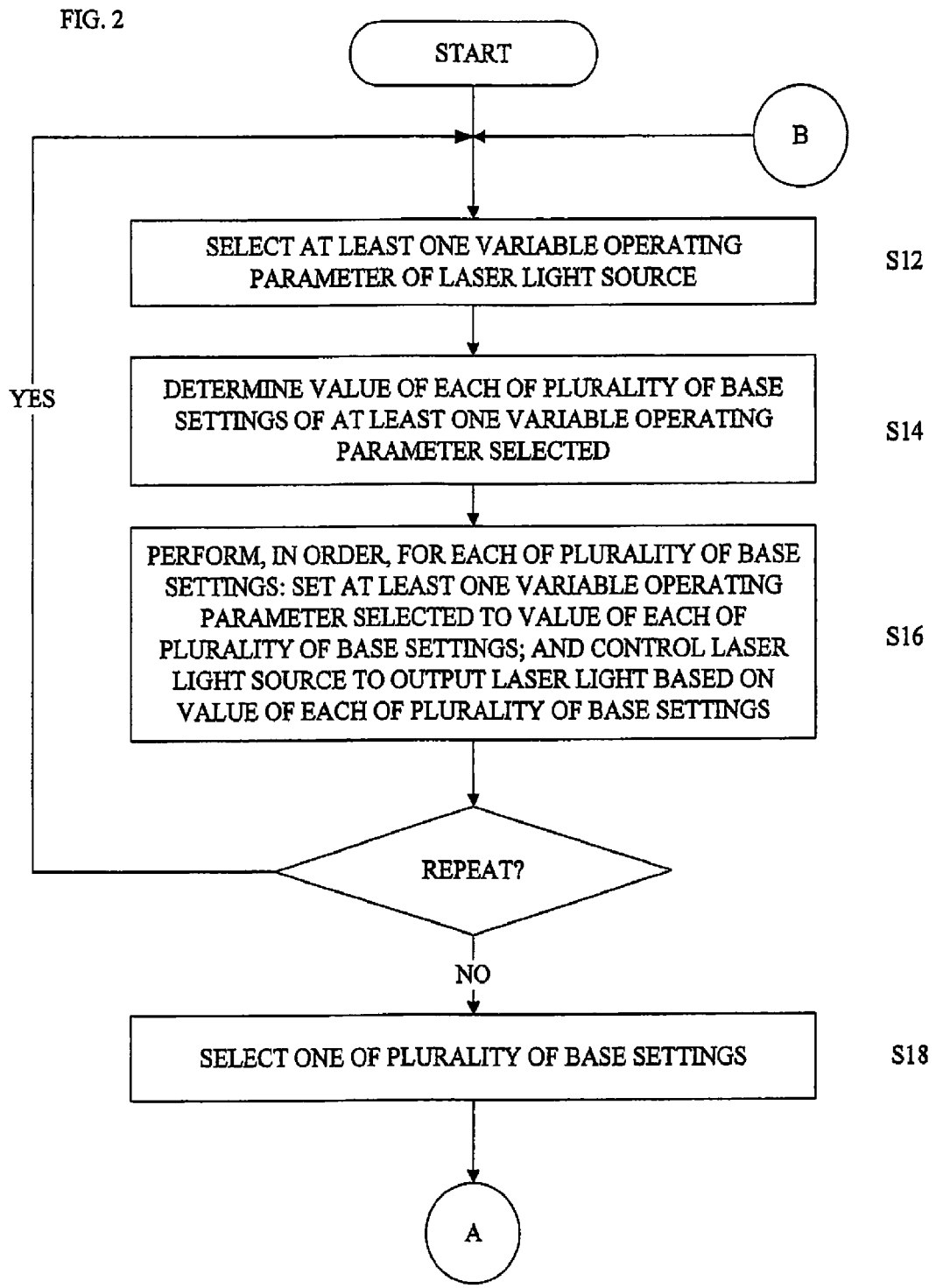
FIG. 2 is a flowchart of steps performed by a controller according to an embodiment of the present invention.

As shown in FIG. 2, the controller 32 can perform one or more iterations of a first process.

Each iteration of the first process can include steps S12 to S16.

At step S12, the controller 32 can select at least one variable operating parameter of the laser light source 22 of the lithotripsy device 20. The at least one variable operating parameter of the laser light source 22 can include one or more of, for example, energy (E) of the laser light output by the laser light source 22, peak power ($P_{peak}$) of the laser light output by the laser light source 22, pulse width (PW) of the laser light output by the laser light source 22, average power ($P_{avg}$) of the laser light output by the laser light source 22, and frequency (F) of the laser light output by the laser light source 22.

At Step S14, the controller 32 can determine a value of each of a plurality of base settings of the at least one variable operating parameter selected.

At Step S16, the controller 32 can perform, in order, for the each of the plurality of base settings, setting the at least one variable operating parameter selected to the value of the each of the plurality of base settings, and controlling the laser light source 22 to output laser light at the calculus C based on the value of the each of the plurality of base settings set.

After performing one or more iterations of the first process, the controller 32 can, at Step S18, select one of the plurality of base settings of the at least one variable operating parameter selected.

Figure 3:
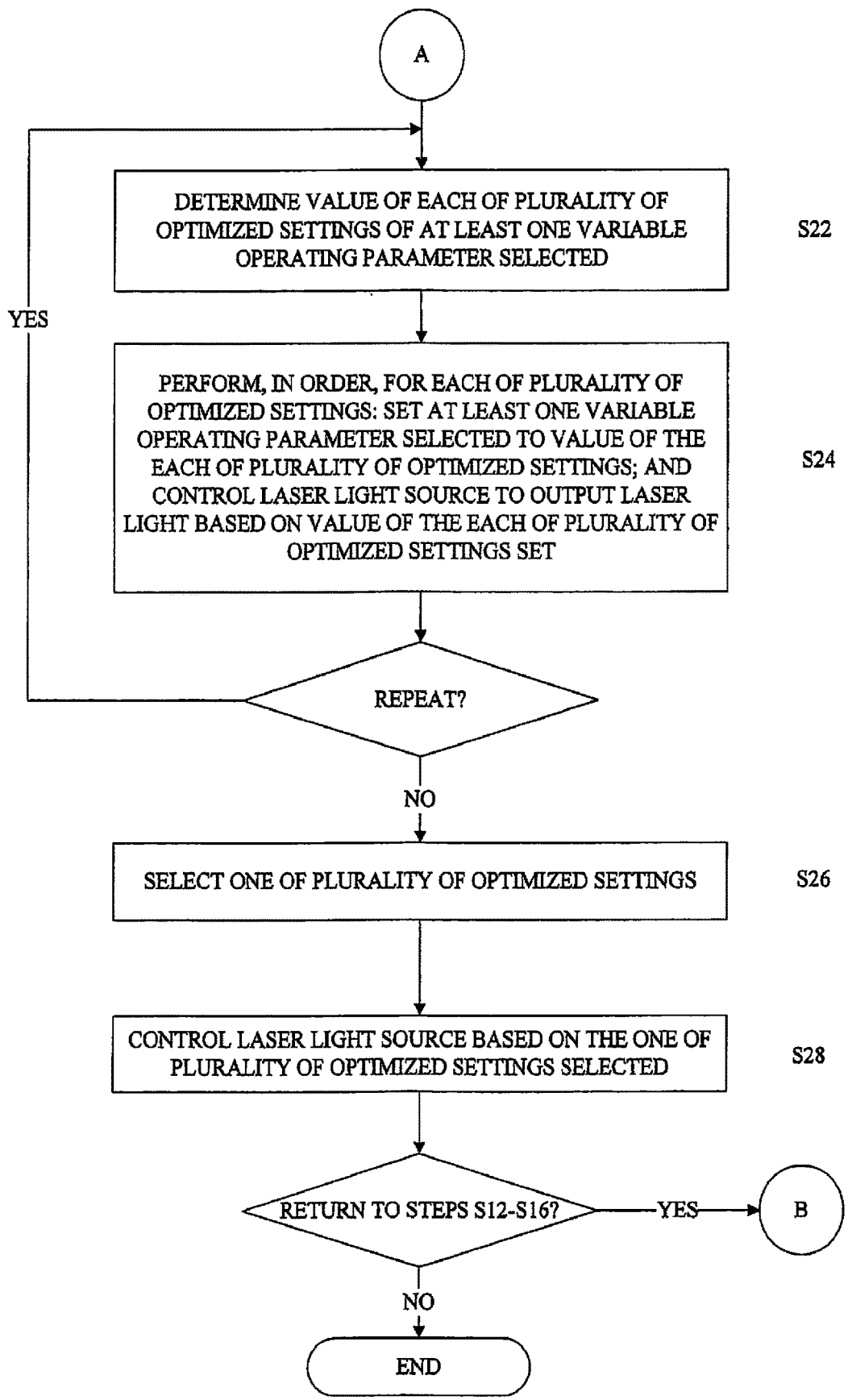
FIG. 3 is a flowchart of additional steps performed by the controller according to an embodiment of the present invention.

Next, as shown in FIG. 3, the controller 32 can perform one or more iterations of a second process.

Each iteration of the second process can include Steps S22 and S24.

At Step S22, the controller 32 can determine a value of each of a plurality of optimized settings of the at least one variable operating parameter selected based on the one of the plurality of base settings of the at least one variable operating parameter selected.

At Step S24, the controller 32 can perform, in order, for the each of the plurality of optimized settings, setting the at least one variable operating parameter selected to the value of the each of the plurality of optimized settings, and controlling the laser light source 22 to output laser light at the calculus C based on the value of the each of the plurality of optimized settings set.

After performing one or more iterations of the second process, the controller 32 can, at Step S26, select one of the plurality of optimized settings of the at least one variable operating parameter selected based on the change in the characteristic of the target object determined.

Next, at Step S28, the controller 32 can control the laser light source 22 to output laser light at the calculus C based on the one of the plurality of optimized settings of the at least one variable operating parameter selected.

Following Step S28, the controller 32, together with the image sensor 16, can generate one or more images of the calculus C that has been treated with the laser light having operating parameters optimized by the first and second processes. The controller 32 can control the display 36 to display the one or more images to allow the user, viewing the one or more images, to determine whether one layer of the calculus C having one mechanical property has been removed by being fragmented or broken to reveal another layer of the calculus C having a different mechanical property that can be more efficiently fragmented or broken under a different optimized setting.

Following Step S28, the input device 34 can receive one or more inputs from the user, and output one or more instructions to the controller 32 based on the one or more inputs. Further, the controller 32 can determine, based on the one or more instructions, whether the user has instructed to return to Steps S12 to S16 for determination of the values of each of a plurality of base settings that are more suitable for fragmenting or breaking the another layer of the calculus C. If returning to Steps S12 to S16 is instructed, the controller 32 can execute Steps S12 to S16 again. If returning to Steps S12 to S16 is not desired, the above-described process ends.

Next, details of Steps S12-S28 will be described by way of examples.

First Example

The details of Steps S12-S28 will be described below by way of a first example.

At Step S12, the input device 34 can receive one or more inputs from the user and output one or more instructions corresponding to the one or more inputs to the controller 32. At Steps S12 and S14, the controller 32 can receive the one or more instructions from the input device 34, select the peak power $P_{peak}$ (or the pulse width PW) of the laser light output by the laser light source 22 as the variable operating parameter based on the one or more instructions received from the input device 34, and determine a value of each of a plurality of base settings of the peak power $P_{peak}$ (or the pulse width PW) of the laser light.

The controller 32 can determine the value of each of the plurality of base settings of the peak power $P_{peak}$ of the laser light based on the one or more instructions received from the input device 34.

The one or more instructions received from the input device 34 can indicate a first range (that is, an upper limit and a lower limit) of values of the peak power $P_{peak}$ of the laser light. The controller 32 can then determine the value of each of the plurality of base settings of the peak power $P_{peak}$ of the laser light that falls within the first range of the values of the peak power $P_{peak}$ of the laser light indicated by the one or more instructions. Moreover, the controller 32 can determine the value of the each of the plurality of base settings of the peak power $P_{peak}$ to be evenly distributed within the first range of values of the peak power $P_{peak}$.

In a modification of the first example, the input device 34 can receive one or more inputs indicating values of each of the plurality of base settings of the peak power $P_{peak}$ within the first range, and output one or more instructions corresponding to the one or more inputs to the controller 32. The controller 32 can then determine the value of each of the plurality of base settings of the peak power $P_{peak}$ of the laser light based on the one or more instructions received from the input device 34.

At Step S16, the controller 32 can perform, in order, for each of the plurality of base settings, setting the peak power $P_{peak}$ the laser light to the value of the each of the plurality of base settings, and controlling the laser light source 22 to output the laser light having the peak power $P_{peak}$ set to the value of the each of the plurality of base settings towards the calculus C to try to or begin to fragment or break the calculus C.

After performing a first iteration of the first process (including Steps S12-S16), the controller 32 can perform a second or subsequent iteration of the first process. In the second or subsequent iteration of the first process, the controller 32 can select another variable operating parameter such as the frequency F of the laser light output by the laser light source 22 and proceed through Steps S14 and S16 based on the selection of the frequency F of the laser light as the variable operating parameter of the laser light.

At Step S18, the controller 32, together with the image sensor 16, can generate one or more images of the calculus C having been treated by the different laser lights having peak power $P_{peak}$ set at the value of the each of the plurality of base settings. The controller 32 can control the display 36 to display the one or more images generated to allow the user to judge the efficacy of each of the different laser lights to fragment or break the calculus C.

Further, at Step S18, the input device 34 can receive one or more inputs from the user (having reviewed the one or more images of the calculus C displayed on the display 36) and output one or more instructions corresponding to the one or more inputs to the controller 32. The controller 32 can then select one of the plurality of base settings of the peak power $P_{peak}$ of the laser light in accordance with the user's one or more inputs. The one of the plurality of base settings of the peak power $P_{peak}$ selected indicates the user's determination, based on the one or more images of the calculus C displayed on the display 36, that the one of the plurality of base settings of the peak power $P_{peak}$ is the most effective amongst the plurality of base settings for fragmenting or breaking the calculus C.

At Step S22, the controller 32 can determine a value of each of a plurality of optimized settings of the peak power $P_{peak}$ of the laser light based on the one of the plurality of base settings selected in Step S18.

Here, the controller 32 can set a second range (that is an upper limit and a lower limit) of the peak power $P_{peak}$ of the laser light, where the second range is smaller than the first range established in Step S14. The controller 32 can then determine the value of each of the plurality of optimized settings of the peak power $P_{peak}$ of the laser light that falls within the second range of the peak power $P_{peak}$ of the laser light. Moreover, the controller 32 can determine the value of the each of the plurality of optimized settings of the peak power $P_{peak}$ to be evenly distributed within the second range of the peak power $P_{peak}$.

At Step S24, the controller 32 can perform, in order for each of the plurality of optimized settings, setting the peak power $P_{peak}$ of the laser light to the value of the each of the plurality of optimized settings of the peak power $P_{peak}$, and controlling the laser light source 22 to output laser light based on the value of the each of the plurality of optimized settings set.

At Step S26, the controller 32, together with the image sensor 16, can generate one or more images of the calculus C having been treated by the different laser lights having peak power $P_{peak}$ set at the value of the each of the plurality of optimized settings. The controller 32 can control the display 36 to display the one or more images generated to allow the user to judge the efficacy of the different laser lights to fragment or break the calculus C.

Further, at Step S26, the input device 34 can receive one or more inputs from the user (having reviewed the one or more images of the calculus C displayed on the display 36) and output one or more instructions corresponding to the one or more inputs to the controller 32. The controller 32 can then select one of the plurality of optimized settings of the peak power $P_{peak}$ of the laser light in accordance with the user's one or more inputs. The one of the plurality of optimized settings of the peak power $P_{peak}$ selected indicates the user's determination, based on the one or more images of the calculus C displayed on the display 36 that the one of the plurality of optimized settings of the peak power $P_{peak}$ is the most effective amongst the plurality of optimized settings for fragmenting or breaking the calculus C.

At Step S28, the controller 32 can further control the laser light source 22 based on the one of the plurality of optimized settings of the peak power $P_{peak}$ of the laser light selected to more effectively and efficiently fragment or break the calculus C.

Second Example

The details of Steps S12-S28 will be described below by way of a second example.

The second example differs from the first example in that at Steps S12 and S14, the controller 32 can receive the one or more instructions from the input device 34, select a plurality of variable operating parameters (instead of a single variable operating parameter as in the first example) based on the one or more instructions received from the input device 34, and determine a value of each of a plurality of base settings of the plurality of operating parameters of the laser light.

Referring to EQUATION 1 discussed above, the controller 32 can select the peak power $P_{peak}$ and the pulse width PW of the laser light as the plurality of variable operating parameters.

Figure 4:
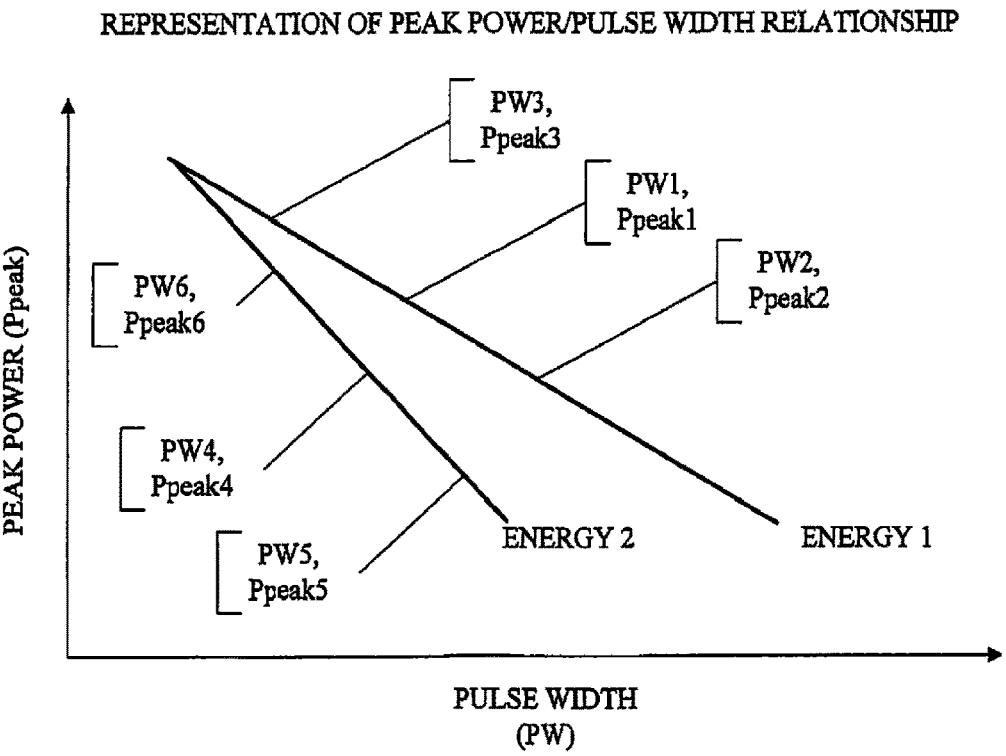
FIG. 4 is a graph illustrating determination of a value of each of a plurality of base settings of at least one variable operating parameter selected according to an embodiment of the present invention.

Further, as shown in FIG. 4, the controller 32 can determine a value of each of a plurality of base settings of the peak power $P_{peak}$ and the pulse width PW of the laser light. Specifically, the controller 32 can determine combinations of values of the peak power $P_{peak}$ and the pulse width PW which will allow the energy E of the laser light to be constant. For example, the controller 32 can determine, for a first base setting, the value of the peak power $P_{peak}$ to be $P_{peak1}$ and the value of the pulse width PW to be PW1, where the laser light output under the operating parameters of the peak power $P_{peak}$ having a value of $P_{peak1}$ and the pulse width PW having a value of PW1 will have a predetermined energy Energy1.

The controller 32 can further determine for a second base setting, the value of the peak power $P_{peak}$ to be $P_{peak2}$ and the value of the pulse width PW to be PW2, where $P_{peak2}$ is less than $P_{peak1}$, where PW2 is greater than PW1, and where the laser light output under the operating parameters of the peak power $P_{peak}$ having a value of $P_{peak2}$ and the pulse width PW having a value of PW2 will have the same predetermined energy Energy1.

The controller 32 can further determine for a third base setting, the value of the peak power $P_{peak}$ to be $P_{peak3}$ and the value of the pulse with PW to be PW3, where $P_{peak3}$ is greater than $P_{peak1}$, where PW3 is less than PW1, and where the laser light output under the operating parameters of the peak power $P_{peak}$ having a value of $P_{peak3}$ and the pulse width PW having a value of PW3 will have the same predetermined energy Energy1.

In a second or subsequent iteration of the first process, the controller 32 can determine combinations of values of the peak power $P_{peak}$ and the pulse width PW of the laser light that will allow the laser light to have a predetermined energy Energy2, where Energy2 is different from Energy1.

In the second or subsequent iteration of the first process, the controller 32 can also select other variable operating parameters. For example, the controller 32 can, referring to EQUATION 2 discussed above, select the frequency F and the pulse width PW as the plurality of variable operating parameters.

Further, referring to Equation 2, the controller 32 can determine a value of each of a plurality of base settings of the frequency F and the pulse width PW of the laser light. Specifically, the controller 32 can determine combinations of values of the frequency F and the pulse width PW which will allow the average power $P_{avg}$ of the laser light to be constant. In this example, referring to EQUATION 2, the controller 32 maintains the peak power $P_{peak}$ of the laser light to be unchanged based on evidence that high peak powers are more at fragmenting or breaking the calculus C.

The second example is similar to the first example in that the controller 32 can determine the value of the each of the plurality of base settings of the plurality of operating parameters to be within the first range of values. Specifically, the controller 32 can determine $P_{peak1}$, $P_{peak2}$ and $P_{peak3}$ to be within a first range of peak power values, and determine PW1, PW2 and PW3 to be within first range of pulse width values.

The second example further differs from the first example in that at Step S22 the controller 32 can determine a value of each of a plurality of optimized settings of the plurality of operating parameters of the laser light.

Figure 5:
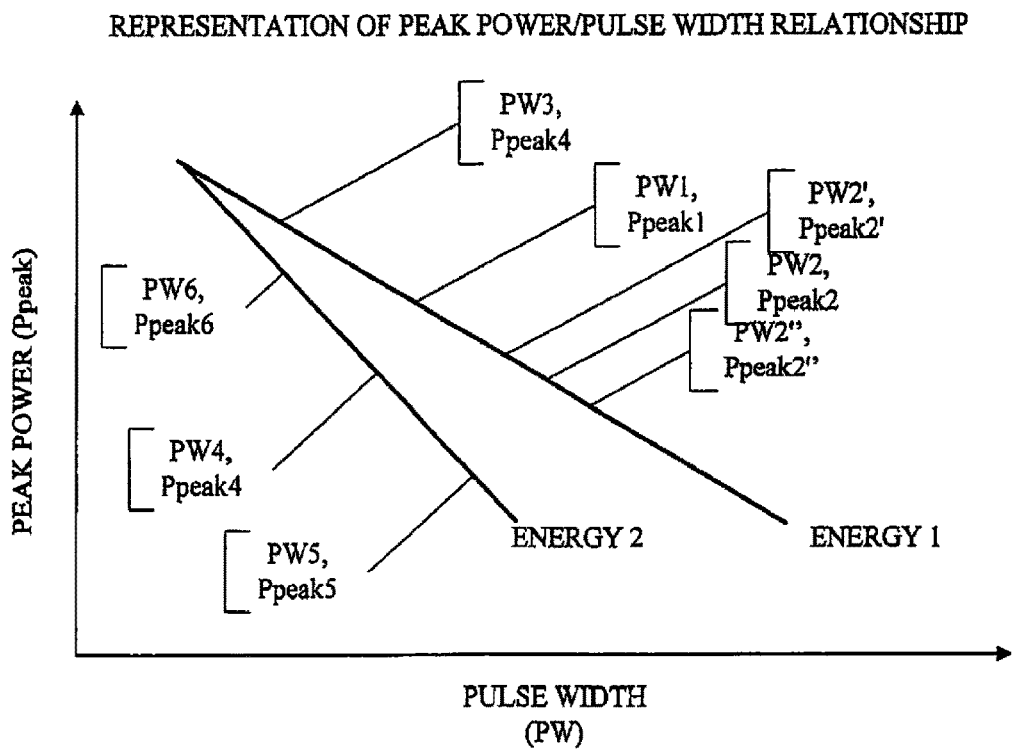
FIG. 5 is a graph illustrating determination of a value of each of a plurality of optimized settings of at least one variable operating parameter selected according to an embodiment of the present invention.

Further, as shown in FIG. 5, the controller 32 can, referring to EQUATION 1 discussed above, determine the value of each of a plurality of optimized settings of the peak power $P_{peak}$ and the pulse width PW of the laser light based on the selection of the base setting having values $P_{peak2}$ and PW2 in Step S18. Specifically, the controller 32 can determine combinations of values of the peak power $P_{peak}$ and the pulse width PW which will allow the energy E of the laser light to be constant. For example, the controller 32 can determine, for a first optimized setting, the value of the peak power $P_{peak}$ to be $P_{peak2}$ and the value of the pulse width PW to PW2, where the laser light output under the operating parameters of the peak power $P_{peak}$ having a value of $P_{peak2}$ and the pulse width PW having a value of PW2 will have the predetermined energy Energy1.

The controller 32 can further determine for a second optimized setting, the value of the peak power $P_{peak}$ to be $P_{peak2}$ and the value of the pulse width PW to be PW2' where $P_{peak2'}$ is greater than $P_{peak2}$, where PW2' is less than PW2, and where the laser light output under the operating parameters of the peak power $P_{peak}$ having value of $P_{peak2'}$ and the pulse with PW having a value of PW2' will have the same predetermined energy Energy1.

The controller 32 can further determine for a third optimized setting, the value of the peak power $P_{peak}$ to be $P_{peak2''}$ and the value of the pulse width PW to be PW2'' where $P_{peak2''}$ is less than $P_{peak2}$, where PW2'' is greater than PW2, and where the laser light output under the operating parameters of the peak power $P_{peak}$ having value of $P_{peak2''}$ and the pulse with PW having a value of PW2'' will have the same predetermined energy Energy1.

Third Example

The details of Steps S12-S28 will be described below by way of a third example.

The third example differs from the second example in that one or more of Steps S12, S14, S18, S22 and S26 can be performed in accordance with a characteristic of the calculus C detected by a sensor.

In Steps S12 and S14, the controller 32 can, together with the image sensor 16, generate one or more images of the calculus C. The controller 32 can further process the one or more images of the calculus C to detect one or more characteristics of the calculus C. The one or more characteristics of the calculus C can include, but is not limited to, the size of the calculus C, the color of the calculus C, and the outer geometry of the calculus C. Further, the controller 32 can select the at least one variable operating parameters of the laser light based on the one or more characteristics of the calculus C detected. Still further, the controller 32 can determine a value of each of a plurality of base settings of the at least one variable operating parameter selected based on the one or more characteristics of the calculus C detected. An an example, in Step S12, the controller 32 can, in response to determining the size of the calculus C to be above a predetermined size set energy E to a higher predetermined value, select peak power $P_{peak}$ and pulse width PW to be the at least one variable operation parameter, and determine the value of the of the plurality of base settings that satisfy Equation 1.

The memory of the controller 32 can also store predetermined relationships between one or more characteristics and corresponding at least one variable operating parameters of the laser light. The controller 32 can then consider the one or more characteristics of the calculus C detected in view of the stored predetermined relationships in order to select the at least one variable operating parameter in Step S12 and to determine the value of the each of the plurality of base settings of the at least one variable operating parameter selected in Step S14.

In Step S18, the controller 32 can, together with the image sensor 16, generate one or more images of the calculus C after treating the calculus C with the laser light according to Steps S12-S16. The controller 32 can further process the one or more images of the calculus C to detect one or more characteristics of the calculus C. The one or more characteristics of the calculus C can include, but is not limited to, a change in the size of the calculus C, a change in the color of the calculus C, and a change in the outer geometry of the calculus C. The controller 32 can further select one of the plurality of base settings based on the one or more characteristics of the calculus C detected. As an example, in Step S18, the controller 32 can determine an image showing a greatest reduction in size of the calculus C, determine the one of the plurality of base settings resulting in the greatest reduction in size of the calculus C and select the one of the plurality of base settings determined.

In Step S22, the controller 32 can, together with the image sensor 16, generate one or more images of the calculus C. The controller 32 can further process the one or more images of the calculus C to detect one or more characteristics of the calculus C. The one or more characteristics of the calculus C can include, but is not limited to, the size of calculus C, the color of the calculus C, and the outer geometry of the calculus C. Further, the controller 32 can determine a value of each of a plurality of optimized settings of the at least one variable operating parameter selected based on the one or more characteristics of the calculus C detected.

In Step S26, the controller 32 can, together with the image sensor 16, generate one or more images of the calculus C after treating the calculus C with the laser light according to Steps S22 and S24. The controller 32 can further process the one or more images of the calculus C to detect one or more characteristics of the calculus C. The one or more characteristics of the calculus C can include, but is not limited to, a change in the size of the calculus C, a change in the color of the calculus C, and a change in the outer geometry of the calculus C. The controller 32 can further select one of the plurality of optimized settings based on the one or more characteristics of the calculus C detected. As an example, in Step S26, the controller 32 can determine an image showing a greatest reduction in size of the calculus C, determine the one of the plurality of optimized settings resulting in the greatest reduction in size of the calculus C and select the one of the plurality of optimized settings determined.

After Step S28, the controller 32 can, together with the image sensor 16, generate one or more images of the calculus C after treating the calculus C with the laser light according to Step S28. The controller 32 can further process the one or more images of the calculus C to detect one or more characteristics of the calculus C. The controller 32 can further determine whether to return to Steps S12-S16 based on the one or more characteristics of the calculus C detected. As an example, the controller 32 can further determine to return to Steps S12-S16 based on a determination that a change in the size of the calculus C is at or below a predetermined threshold, or that the a change in the color of the calculus C is at or below a predetermined amount.

In the description provided above, the functions of generating and processing images, and the functions of controlling the laser light source 22 are described as being performed by the controller 32. However, it is understood that the functions of generating and processing images and the functions of controlling the laser light source 22 can be performed by separate controllers in communication with each other.

Another embodiment of the present invention includes a method performed by the controller 32 described above.

Still, another embodiment of the present invention includes a computer-readable storage device storing instructions that can cause a processor comprising hardware of the controller 32 to perform the functions described above.

In the technique described above, after Step S18, one of the plurality of base settings of the peak power $P_{peak}$ (or another variable operating parameter) of the laser light output by the laser light source 22 that is more effective for fragmenting or breaking the calculus C having a particular mechanical property corresponding the one of the plurality of base settings is selected to more effectively fragment or break the calculus C having the particular mechanical property. Such a selection in Step S18 represents an improvement over conventional lithotripsy techniques. Further, after Step S28, selecting one of the plurality of optimized settings allows for even more effective fragmenting or breaking of the calculus C. Such a selection in Step S28 represents an additional improvement over conventional lithotripsy techniques.

While embodiments of the present invention have been described, it will, of course, be understood that various modifications and changes in form or detail could readily be made without departing from the spirit of the invention. It is therefore intended that the invention be not limited to the exact forms described and illustrated, but should be construed to cover all modifications that may fall within the scope of the appended claims.

What is claimed is:

1. A system comprising:
  a controller configured to:
    perform one or more iterations of a first process, wherein in the first process the controller is configured to:
      select at least one variable operating parameter of a laser light source of a lithotripsy device;
      determine a value of each of a plurality of base settings of the at least one variable operating parameter selected; and
      perform, in order, for the each of the plurality of base settings:
        set the at least one variable operating parameter selected to the value of the each of the plurality of base settings; and
        control the laser light source to output laser light based on the value of the each of the plurality of base settings set;
      select one of the plurality of base settings of the at least one variable operating parameter selected; and
    perform one or more iterations of a second process, wherein in the second process, the controller is configured to control the laser light source based on the one of the plurality of base settings of the at least one variable operating parameter selected by being configured to:
      determine a value of each of a plurality of optimized settings of the at least one variable operating parameter, the plurality of optimized settings each representing a variation of the selected base setting different than each of the plurality of base settings in the first process; and
      perform, in order, for the each of the plurality of optimized settings:
        set the at least one variable operating parameter selected to the value of the each of the plurality of optimized settings; and
        control the laser light source to output laser light based on the value of the each of the plurality of optimized settings set.

2. The system according to claim 1,
  wherein, in the first process, the controller is configured to determine the value of each of the plurality of base settings of the at least one variable operating parameter to be within a first predetermined range, and
  wherein, in the second process, the controller is configured to determine the value of each of the plurality of optimized settings of the at least one variable operating parameter to be within a second predetermined range that is smaller than the first predetermined range.

3. The system according to claim 1,
  wherein, in the first process, the controller is configured to determine the value of each of the plurality of base settings of the at least one variable operating parameter selected such that an absolute value of a difference in values of one base setting and an adjacent base setting in size order is a first predetermined constant, and
  wherein, in the second process, the controller is configured to:
  determine the value of each of the plurality of optimized settings of the at least one variable operating parameter selected such that the absolute value of the difference in values of one optimized setting and an adjacent optimized setting in size order is a second predetermined constant that is less than the first predetermined constant.

4. The system according to claim 1,
  wherein the controller is configured to:
  control a sensor to:
  detect a characteristic of a target object to be irradiated by the laser light prior to performance of the at least one or more iterations of the second process; and
  detect the characteristic of the target object after performance of the at least one or more iterations of the second process;
  determine a change in the characteristic of the target object from prior to performance of the at least one or more iterations of the second process to after performance of the at least one or more iterations of the second process;
  select one of the plurality of optimized settings of the at least one variable operating parameter selected based on the change in the characteristic of the target object determined; and
  control the laser light source based on the one of the plurality of optimized settings of the at least one variable operating parameter selected.

5. The system according to claim 1,
wherein, in the first process, the controller is configured to select the at least one variable operating parameter of the laser light source of the lithotripsy device by being configured to select at least one of:
energy (E) of the laser light output by the laser light source;
peak power ($P_{peak}$) of the laser light output by the laser light source;
pulse width (PW) of the laser light output by the laser light source;
average power ($P_{avg}$) of the laser light output by the laser light source; and
frequency (F) of the laser light output by the laser light source,
as the at least one variable operating parameter.

6. The system according to claim 1,
wherein, in the first process, the controller is configured to select the at least one variable operating parameter of the laser light source of the lithotripsy device by being configured to:
select peak power ($P_{peak}$) of the laser light output by the laser light source and pulse width (PW) of the laser light output by the laser light source, as the at least one variable operation parameter, where energy (E) of the laser light output by the laser light source is related to $P_{peak}$ and PW according to Equation 1: $E=P_{peak}*PW$, or
select PW and frequency (F) of the laser light output by the laser light source, as the at least one variable operation parameter, where average power ($P_{avg}$) of the laser light output by the laser light source is related to $P_{peak}$, PW and F according to Equation 2: $P_{avg}=P_{peak}*PW*F$, and
wherein, in the first process, the controller is configured to determine the value of the each of the plurality of base settings of the at least one variable operation parameter selected by being configured to:
in response to selecting $P_{peak}$ and PW as the at least one variable operation parameter, determine a plurality of combinations of a value of $P_{peak}$ and a value of PW such that E in Equation 1 is constant across the plurality of combinations of the value of $P_{peak}$ and the value of PW; and
in response to selecting PW and F as the at least one variable operation parameter, determine a plurality of combinations of a value of PW and a value of F such that $P_{avg}$ and $P_{peak}$ in Equation 2 are constant across the plurality of combinations of the value of PW and the value of PW.

7. The system according to claim 1,
wherein, in the first process, the controller is configured to determine the value of each of the plurality of base settings of the at least one variable operating parameter to be within a first predetermined range.

8. The system according to claim 1,
wherein, in the first process, the controller is configured to determine the value of each of the plurality of base settings of the at least one variable operating parameter selected such that an absolute value of a difference in values of one base setting and an adjacent base setting in size order is a first predetermined constant.

9. The system according to claim 1,
wherein the controller is configured to select the one of the plurality of base settings of the at least one variable operating parameter selected based on a received user selection.

10. The system according to claim 1,
wherein the controller is configured to:
control a sensor to detect a characteristic of a target object prior to performance of the at least one or more iteration of the first process; and
in performing the one or more iterations of the first process, select the at least one variable operating parameter of the laser light source, determine the value of the each of the plurality of base settings of the at least one variable operating parameter selected, or both based on the characteristic of the target object detected by the sensor.

11. The system according to claim 1,
wherein the controller is configured to:
control a sensor to:
detect a characteristic of a target object to be irradiated by the laser light prior to performance of the at least one or more iterations of the first process; and
detect the characteristic of the target object after performance of the at least one or more iterations of the first process;
determine a change in the characteristic of the target object from prior to performance of the at least one or more iterations of the first process to after performance of the at least one or more iterations of the first process; and
select the one of the plurality of base settings of the at least one variable operating parameter selected based on the change in the characteristic of the target object determined.

12. The system according to claim 1, further comprising:
the lithotripsy device.

13. A method comprising:
performing one or more iterations of a first process, wherein the first process comprises:
selecting at least one variable operating parameter of a laser light source of a lithotripsy device;
determining a value of each of a plurality of base settings of the at least one variable operating parameter selected; and
performing, in order, for the each of the plurality of base settings:
setting the at least one variable operating parameter selected to the value of the each of the plurality of base settings; and
controlling the laser light source to output laser light based on the value of the each of the plurality of base settings set;
selecting one of the plurality of base settings of the at least one variable operating parameter selected; and
performing one or more iterations of a second process, wherein the second process comprises controlling the laser light source based on the one of the plurality of base settings of the at least one variable operating parameter selected, including:
determining a value of each of a plurality of optimized settings of the at least one variable operating parameter, the plurality of optimized settings each representing a variation of the selected base setting different than each of the plurality of base settings in the first process; and
performing, in order, for the each of the plurality of optimized settings:
setting the at least one variable operating parameter selected to the value of the each of the plurality of optimized settings; and controlling the laser light source to output laser light based on the value of the each of the plurality of optimized settings set.

14. A computer-readable storage device storing instructions that cause a computer of a controller to:

perform one or more iterations of a first process, wherein in the first process the computer is configured to:

select at least one variable operating parameter of a laser light source of a lithotripsy device;

determine a value of each of a plurality of base settings of the at least one variable operating parameter selected; and perform, in order, for the each of the plurality of base settings:

set the at least one variable operating parameter selected to the value of the each of the plurality of base settings; and control the laser light source to output laser light based on the value of the each of the plurality of base settings set;

select one of the plurality of base settings of the at least one variable operating parameter selected; and perform one or more iterations of a second process, wherein in the second process, the computer is configured to control the laser light source based on the one of the plurality of base settings of the at least one variable operating parameter selected by being configured to:

determine a value of each of a plurality of optimized settings of the at least one variable operating parameter, the plurality of optimized settings each representing a variation of the selected base setting different than each of the plurality of base settings in the first process; and in order, for the each of the plurality of optimized settings:

set the at least one variable operating parameter selected to the value of the each of the plurality of optimized settings; and control the laser light source to output laser light based on the value of the each of the plurality of optimized settings set.

* * * * *

UNITED STATES PATENT AND TRADEMARK OFFICE
CERTIFICATE OF CORRECTION

PATENT NO. : 12,059,204 B2
APPLICATION NO. : 16/968801
DATED : August 13, 2024
INVENTOR(S) : Talbot et al.

It is certified that error appears in the above-identified patent and that said Letters Patent is hereby corrected as shown below:

On the Title Page

In item (57), in "Abstract", in Column 2, Line 4, delete "process," and insert --process-- therefor On page 2, in Column 1, under "Abstract", Line 2, delete "selected" and insert --selected,-- therefor Signed and Sealed this
Fifth Day of August, 2025

Coke Morgan Stewart
*Acting Director of the United States Patent and Trademark Office*